United States Patent
Liotta et al.

(10) Patent No.: US 7,794,952 B2
(45) Date of Patent: Sep. 14, 2010

(54) BIOMARKER ISOLATION AND USE THEREOF TO CHARACTERIZE PHYSIOLOGICAL STATE

(75) Inventors: Lance Liotta, Bethesda, MD (US); Emanuel Petricoin, Gainesville, VA (US)

(73) Assignee: George Mason University, Fairfax, VA (US)

( * ) Notice: Subject to any disclaimer, the term of this patent is extended or adjusted under 35 U.S.C. 154(b) by 468 days.

(21) Appl. No.: 11/639,414

(22) Filed: Dec. 15, 2006

(65) Prior Publication Data

US 2007/0275483 A1    Nov. 29, 2007

Related U.S. Application Data

(60) Provisional application No. 60/750,376, filed on Dec. 15, 2005.

(51) Int. Cl.
*G01N 33/53* (2006.01)
(52) U.S. Cl. .................. 435/7.1; 436/501; 436/518; 422/50; 530/300; 530/350
(58) Field of Classification Search ........... None
See application file for complete search history.

(56) References Cited

OTHER PUBLICATIONS

Lowenthal et al., Clinical Chemistry, vol. 51, No. 10, pp. 1933-1945, 2005.*
M.S. Lowenthal et al., Analysis of Albumin-Associated Peptides and Proteins from Ovarian Cancer Patients, Clinical Chemistry, Oct. 2005, pp. 1933-1945, vol. 51 issue 10.
K.A. Tubbs et al., Detection and Quantification of b-2-Microglobulin Using Mass Spectrometric Immunoassay, Analytical Biochemistry, Feb. 2001, pp. 26-35, vol. 289 issue 1.
E.F. Petricoin et al., SELDI-TOF-Based Serum Proteomic Pattern Diagnostics for Early Detection of Cancer, Current Opinion in Biotechnology, Feb. 2004, pp. 24-30, vol. 15 issue 1.

* cited by examiner

*Primary Examiner*—Lisa V Cook
(74) *Attorney, Agent, or Firm*—Millen, White, Zelano, Branigan, P.C.

(57) ABSTRACT

The present invention relates to compositions and methods for characterizing the physiological state of a living system, including cells, tissues, organs, and whole organisms. The methods involve capturing biomarkers from the living system, and correlating their presence or absence to a physiological state. The biomarkers can be captured from the system, and then detected using any suitable analytical system to determine their presence or absence. In one embodiment, the invention relates to a method of detecting a polypeptide biomarker in a blood serum or plasma sample obtained from a single subject with an affinity ligand which is capable of binding to a plurality of different polypeptide biomarkers derived from the same parental molecule.

13 Claims, 2 Drawing Sheets

| Amino Acids | BRCA2 Sequence | Detected in High Risk Pool | Detected in Stage I Pool | Detected in Stage II-III Pool |
|---|---|---|---|---|
| 965-981 | MTLGQDLKSDISLNIDK | | X | X |
| 1942-1959 | VSKISPCDVSLETSDICK | X | X | |
| 2390-2401 | NEKMRHLITTGR | X | | |
| 2447-2459 | NKINDNEIHQFNK | X | | X |

B

US 7,794,952 B2

BIOMARKER ISOLATION AND USE THEREOF TO CHARACTERIZE PHYSIOLOGICAL STATE

CROSS-REFERENCE TO RELATED APPLICATIONS

This application claims the benefit of U.S. Provisional Application Ser. No. 60/750,376, filed Dec. 15, 2005 which is incorporated herein by reference in its entirety.

REFERENCE TO SEQUENCE LISTING

This application contains a Sequence Listing submitted in electronic and print form. The electronic and print form of the Sequence Listing are identical to each other pursuant to 37 CFR §1.52(e) (4), contains the following file: "GMU0030.txt", having a size in bytes of 2 KB, recorded on Jan. 19, 2010. The information contained in the sequence listing is hereby incorporated by reference in its entirety pursuant to 37 CFR §1.52(e) (5).

SUMMARY OF THE INVENTION

The present invention relates to compositions and methods for characterizing the physiological state of a living system, including cells, tissues, organs, and whole organisms. The methods involve capturing biomarkers from the living system, and correlating their presence or absence to a physiological state. The biomarkers can be captured from the system, and then detected using any suitable analytical system to determine their presence or absence.

Any physiological state can be characterized in accordance with the present invention, including disease; disease predisposition; disease status (e.g., stage; active; symptomatic; inactive; asymptomatic); and cell, tissue, organ, or system status (e.g., state of the circulatory system; state of the immune system; state of the excretory system, such as the kidney; state of the heart; etc.). Diseases include cancer; diseases mediated by infectious agents, such as viruses, bacteria, fungi, and protista; degenerative diseases; etc.

In one embodiment of the present invention, the methods relate to detecting the presence or absence of a biomarker in a blood serum or plasma sample from a subject, comprising capturing at least one biomarker from the blood serum or plasma sample, and detecting its presence or absence.

In another aspect, the invention relates to a method of detecting the presence or absence of a polypeptide biomarker in a blood serum or plasma sample from a subject, comprising:
a) capturing at least one polypeptide biomarker from a blood serum or plasma sample with an affinity ligand which is capable of binding to a plurality of different polypeptide biomarkers derived from the same parental molecule, wherein said sample is obtained from a single subject; and
b) detecting the presence or absence of at least one polypeptide biomarker captured by the affinity ligand.

In another aspect, the invention relates to a method of detecting the presence or absence of a biomarker in a blood serum or plasma sample from a subject, comprising:
a) capturing at least one biomarker from a blood serum or plasma sample with an affinity ligand which is capable of binding to a plurality of different biomarkers derived from the same parental molecule, wherein said sample is obtained from a single subject; and
b) detecting the presence or absence of at least one biomarker captured by the affinity ligand.

In another aspect, the invention relates to a method of detecting the presence or absence of a biomarker in a blood serum or plasma sample from a subject, comprising:
a) capturing different biomarkers from a blood serum or plasma sample with a plurality of different affinity ligands, wherein each ligand is capable of binding to a different plurality of different biomarkers, and wherein the different biomarkers are derived from the same parental molecule; and
b) detecting the presence or absence of the different biomarkers captured by the different affinity ligands.

In another aspect, the invention relates to a method of detecting ovarian cancer in a subject, comprising detecting the presence or absence of a fragment of a full-length molecule of a BRCA2 polypeptide, wherein the fragment comprises amino acids 965-981 of said BRCA2.

In another aspect, the invention relates to a method of detecting a subject at high risk for ovarian or breast cancer, comprising detecting the presence or absence of a fragment of a full-length molecule of BRCA2 polypeptide, wherein the fragment comprises amino acids 2390-2401 of said BRCA2.

In another aspect, the invention relates to a method of detecting the presence or absence of a polypeptide biomarker in a blood serum or plasma sample from a subject, comprising:
a) capturing albumin from a blood serum or plasma sample from a single patient;
b) dissociating polypeptide biomarkers from said captured serum or plasma albumin; and
c) detecting the presence or absence of at least one polypeptide biomarker dissociated from said albumin.

There is no limitation on the composition of the biomarkers. For example, they can be polypeptides, nucleic acids, carbohydrates, lipids, or combinations thereof. The biomarkers can be entirely endogenously produced, or can be derived from compounds introduced into the system and then optionally processed (e.g., metabolized, digested) by it. There is also no limit on the cellular compartment in which the biomarker is produced and/or resides, as long as it is detectable.

The biomarker can be directly detected without any processing, or it can be subjected to a processing step. This processing can include digestion (e.g., proteolysis using enzymes or chemicals), chemical treatments, and/or the addition of groups to the molecule. In certain embodiments, as explained in more detail in the examples, the biomarkers are subjected to trypsin digestion, and the products are detected and correlated with a disease state. Any proteolytic treatment can be utilized, including enzymes (e.g., trypsin, chymotrypsin; carboxypeptidase; serine proteases; proteinase K; papain; pepsin) and chemical treatments, e.g., CNBR, formic acid etc. A plurality of agents and/or treatments can be utilized. When biomarkers have been captured and sequence analyzed, proteolytic treatments can further be designed based on the knowledge of the sequence, e.g., the presence of proteolytic cleavage sites.

Biomarkers can be captured by any suitable method. In the examples, biomarkers were captured by first isolating a low molecular weight fraction comprising serum albumin, and then the biomarkers that bound to the albumin were detected using mass spectroscopy. Examples of affinity ligands (which can be incorporated into a suitable matrix) that bind to serum albumin, include, e.g., antibodies; and dyes, such as Cibacron Blue and derivatives thereof. After capture via the protein, the biomarkers are separated using routine methods, e.g., elution, precipitation, digestion, etc. In addition to this approach, the present invention provides methods of detecting the biomarkers using affinity ligands which are specific to the biomarker, rather than the carrier protein (e.g., albumin, proteoglycans, and other abundance serum proteins). An affinity ligand is any material which is capable of specifically binding to a biomarker, or a portion thereof. Generally, the affinity ligand has an affinity for the biomarker which is sufficient for the latter to remain bound to it in high concentrations at equilibrium. Examples of affinity ligands include antibodies (single chain, polyclonal, monoclonal, phage-displayed, Fab, recombinant, chimeric, humanized, etc.); aptamers; lectins; polypeptides which associate with the biomarkers; etc.

The affinity ligand can be selected such that it binds to a plurality of different polypeptide biomarkers derived from the same parental molecule. For example, as shown in the examples, multiple ("plurality") and different fragments of BRCA2 ("same parental molecule") were detected after trypsin digestion. When such different fragments contain common regions (e.g., a fragment 1 contains amino acids 1-10; a fragment 2 contains amino acids 6-15), the common region (e.g., residues 6-10) can serve as binding site for an affinity ligand suitable to capture it.

In another embodiment, biomarkers can be captured with a plurality of different affinity ligands, wherein each ligand is capable of binding to a different biomarker plurality, and wherein the different biomarkers are derived from the same parental molecule. For instance, the examples below show three different fragments, each containing a unique region of the parental BRCA2 molecule. Rather than using a single affinity ligand, a ligand to each different sequence can be used for the capture step. For instance, antibodies can be routinely generated to the unique epitopes of the individual fragments.

Capture by the affinity ligand can be accomplished routinely. Methods include, but are not limited to, immunoprecipitation; and coupling the ligand to a matrix, such as agarose, and then contacting the matrices with the sample under conditions effective for the biomarker to stably bind to the ligand.

Samples can be comprised of any material of interest, including, e.g., blood serum; blood plasma; whole blood; cell lysates; cerebrospinal fluid; lymph; fluids in extracellular compartments; urine; feces; ascites; kidney dialysis effluent; wound exudate; semen; seminal fluid; mucous; vitreous fluid; ocular fluid; etc.

The detection of biomarkers can be accomplished using any suitable system, including systems that separate molecules based on size, charge, composition, hydrophobicity, hydrophilicity, degree of glycosylation, or any other physical characteristic. Specific systems include, e.g., gel electrophoresis; mass spectroscopy; size and/or charge exclusion matrices; NMR; spectrometers; etc. Examples of mass spectroscopy systems include, e.g., MALDI-TOF; fast scanning ion cyclotron resonance spectrometry; fast scanning ion cyclotron resonance spectrometry; gas chromatography/mass spectrometry; Fourier-Transform mass spectrometry; accelerator mass spectrometry; chromatograph-combustion-isotope ratio mass spectrometry; inductively coupled argon plasma mass spectrometry; electrospray ionization (ESI) for MS, including orthogonal ESI; etc.

Analysis of the detected biomarkers can be accomplished manually or using software that facilitates the recognition of patterns of biomarkers present in the sample. A single or plurality of biomarkers can be identified and correlated with a physiological state. The biomarkers can be utilized as a unique signature or fingerprint, where the type of biomarker(s) (as well as abundance) can be correlated with a state of the living system.

As indicated in more detail in the examples, BRCA2 and mutations thereof, are known in the art. See, e.g., NM_000059 for a sequence of a wild-type or normal allele. See, also, OMIM, Entry 600185 for BRCA2, for a more complete discussion of normal and disease-associated alleles. All references mentioned here are hereby incorporated by reference in their entirety. As indicated in OMIM, several human diseases that are linked to loss-of-function of BRCA2 have been analyzed using human molecular genetics. These include, but are not limited to breast and ovarian cancer (Lancaster et al., 1996), pancreatic cancer (Schutte et al., 1995), chronic lymphocytic leukemia (CLL) (Garcia-Marco et al., 1996), prostate cancer, (Edwards et al., 2003), cancer of the GI tract (Risch et al., 2001), glioblastoma, medulloblastoma, Acute Lymphoblastic Leukemia (AML), Fanconi anemia, skin cancer, epithelial tumors, etc.

In general, correlation of a particular biomarker plurality presence and/or relative abundance of each in one or more bodily fluids with body states, e.g., a disease state, can be performed using conventional methods with routine experiments, e.g., involving analyses of samples from subjects having known body states of interest Comparing protein expression profiles of a biological sample isolated from a patient of interest and a healthy person is a practical method for identifying clinically relevant markers that may be useful in risk stratification, diagnosis, treatment monitoring, and detection of recurrence. The present invention is based on the discovery and development of a system for identifying protein markers or a pattern of protein markers that indicate a pathological condition or a genetic predisposition to a disease/disorder in a patient. One or more of the identified markers or the pattern of markers can then be used in diagnosis, prognosis, and/or treatment regimens related to the pathological condition or a genetic predisposition of interest.

The invention involves generating a pattern of proteins in a sample using a biometric analysis to identify time-dependent or treatment-dependent differences in the physiological state of the same patient. Methods of the invention are useful to detect cancer in patients, for example.

In one embodiment of the invention, there is provided a method for identifying a marker for cancer comprising: a) collecting a first sample from a cancerous tissue of a cancer patient; b) collecting a second sample from a healthy patient, wherein the first and second samples comprise cancerous and noncancerous tissue samples; c) separating the proteins within each of the samples; and, d) comparing the profiles of proteins from the first and second samples, wherein a difference in the profiles identifies a cancer marker. The profile can then be used to identify the presence or absence of a particular protein in a sample, as well as identify whether the amount of that protein is changed. The present invention concerns identifying one or more markers of cancer based on differences in protein profiles of a paired sample.

In some embodiments of the invention, a difference in a paired sample is detected. Multiple paired samples from different patients are used, in some methods of the invention, to generate a protein pattern based on multiple protein profiles from different patients. A protein pattern is generated by comparing each profile from each patient sample and identifying those spots or proteins that are similarly modulated between the different patient samples or paired samples, thereby accumulating a pattern indicative of cancer that may be used to diagnose development or progression of the disease in any patient sample. Furthermore, the generation of such a pattern could be used as a standard in diagnosing cancer in any patient having cancer.

In still further embodiments, the present invention comprise generating a computer-assisted image of the profiles generated by two-dimensional gel electrophoresis prior to comparing the profiles. These digitalized images may be produced by any method, which are well known to those of skill in the art. The images may be analyzed by direct visualization by a person or by inputting the data into a computerized device that can evaluate it, such as by using a learning algorithm.

In further embodiments a learning algorithm is employed to compare the computer-assisted images of the profiles. In still further embodiments, the learning algorithm is a trained support vector machine. Learning algorithms may be employed not only to compare individual paired samples, but also to compare and analyze multiple paired samples in order to detect a pattern of proteins that identifies a cancer patient. Thus, in additional methods of the invention, multiple paired samples from cancer patients are collected, compared (one sample compared to the other sample in the paired sample), and then analyzed. The method involves analyzing the profiles of the paired samples to identify a pattern of proteins/peptides in which a cancer marker is identified.

In further embodiments, the present invention comprises staining of fluid proteins as part of the 2-D gel electrophoresis process using a variety of protein staining techniques. Methods of the invention involve, in some embodiments, exposing the 2-D electrophoresed gel to silver staining, fluorescent staining, or a colorimetric or enzymatic dye. In further embodiments, the dye is ponceau S, streptavidin-alkaline phosphatase, coomassie blue or ruby red.

A noncancerous sample may be from any tissue, culture, cell, or specimen that is noncancerous. In some embodiments of the invention, a noncancerous sample is blood from a specimen that is not cancerous or that does not have a tumor. A cancerous sample will be tissue, cells, fluid, or other collection from a breast that is cancerous (may initially be only suspected of being cancerous). In certain embodiments of the invention, the sample contains fluid from a particular tissue of interest.

It is contemplated that multiple cancer markers among the cancer proteins may be identified. At least 1, 2, 3, 4, 5, 6, 7, 8, 9, 10 or more cancer markers are identified by methods of the invention. These markers may then be the direct basis for diagnosing, prognosing, or treating a patient with cancer. A sample from a patient suspected of having cancer will be assayed for one or more of the cancer markers using methods well known to those of skill in the art, including immunochemical assays or nucleic acid-based assays. In certain embodiments of the invention, kits for identifying cancer markers identified by methods of the invention are specifically contemplated as part of the invention.

In some embodiments of the invention, there is a method of detecting development or progression of cancer in a patient comprising: a) collecting a sample comprising serum from at least one patient; b) separating serum proteins using routine biochemical techniques; and, c) analyzing the profile of serum proteins from the sample to detect a cancer marker identified by screening methods described above.

Specific fragments of the BRCA-2 protein have been identified in the serum. At least some of these fragments exist bound to serum resident carrier proteins such as albumin. The relative abundance of four distinct fragments of BRCA-2 was found to be distinctly different between sera from patients who were at risk for ovarian and breast cancer versus patients who had stage I non metastatic ovarian cancer, and distinct from patients known to have metastatic ovarian cancer. Measurement of specific combinations of BRCA-2 fragments constitute diagnostic disease markers, and may provide pathophysiologic information relative to choice of therapy or disease outcome. A high throughput means of measuring panels of specific protein fragments is accomplished using antibody capture which binds more than one class of fragments of the same parent molecule such as BRCA-2. All captured species are eluted into an assay device which can detect the fragment and simultaneously measure its size. In one embodiment the assay device is a mass spectrometer.

In one aspect, the invention is drawn to, but not limited to, the detection of the following peptides:

MTLGQDLKSDISLNIDK (SEQ ID NO: 1) (amino acids 965-981 of BRCA2)

VSKISPCDVSLETSDICK (SEQ ID NO: 2) (amino acids 1942-1959 of BRCA2)

NEKMRHLITTGR (SEQ ID NO: 3) (amino acids 2390-2401 of BRCA2)

NKIN DNEIHQFNK (SEQ ID NO: 4) (amino acids 2447-2459 of BRCA2)

BRCA2 is a well-studied tumor suppressor protein related to the p53 pathway that is directly implicated in familial breast cancer and ovarian cancer. Although the role of BRCA2 in breast and ovarian cancer predisposition is poorly understood, it is known that mutations of the BRCA2 gene are responsible for one-third of hereditary breast cancer cases. This invention in part is based on the discovery that a variety of BRCA-2 protein fragments exist in the blood and that distinct subsets of fragments correlate with the patient's disease state. This discovery is completely unexpected at least for the following reasons. (A) BRCA-2 is a large (490 kda) low abundance nuclear cellular protein that is not expected to be shed into the extracellular space, would not be expected to enter the circulation, and would not be expected to be easily detectable because of its low abundance. The relative fragment sizes of BRCA-2 represented in the blood may reflect the tissue enzyme cleavage history and may be directly related to the amino acid sequence mutations that exist in the BRCA-2 proteins being cleaved. Thus genetic BRCA-2 mutations may be represented as specific shed protein fragments. The relative presence or abundance of a particular set of fragments may reflect the pathogenetics of disease. Measurement of specific combinations of BRCA-2 fragments constitute diagnostic disease markers, and may provide pathophysiologic information relative to choice of therapy or disease outcome.

This discovery exemplifies the concept of this invention, namely that subsets of specific protein fragments contain diagnostic information independent from the parent protein molecule from which they are derived. A high throughput means of measuring panels of specific protein fragments is accomplished using antibody capture which binds more than one class of fragments of the same parent molecule such as BRCA-2. All captured species are eluted into an assay device which can detect the fragment and simultaneously measure its size.

Preferably, the BRCA2 fragment-specific antibody reagent is prepared by immunization of a host animal with a suitable immunogen such as an BRCA2 peptide-containing immunogen mixture, e.g., a purified extract of spleen or tumor cells; BRCA2 fragment-expressing transfectant cell lines (see European Patent Publication 346,702); an immunogen conjugate comprising a synthetically prepared peptide coupled to a conventional immunogenic carrier molecule, where the peptide has an amino acid sequence encompassing an epitope of BRCA2 peptide; and the like as will be understood in the art.

Antibody reagents comprising monoclonal antibodies will be generally preferred. Particularly preferred BRCA2 fragment-specific monoclonal antibodies are those which bind to substantially the same BRCA2 motif as defined in the instant invention. It will be understood that a number of standard methods can be used in order to determine whether a particular monoclonal antibody binds to substantially the same epitope or motif. A particularly useful method is competitive binding, wherein the ability of the antibody of interest to bind to BRCA2 fragment in the presence of the reference antibody is measured. Substantial inability of both antibodies to bind simultaneously indicates that substantially the same epitope is involved.

The present invention also provides an improved method for the immunoassay determination of the amount of BRCA2 fragment in a blood sample, e.g. wherein the blood sample is contacted with an antibody reagent that is specific for BRCA2 fragment and binding between the antibody reagent and the levels of said BRCA2 fragment is determined, preferably by sandwich immunoassay. The improvement comprises calibrating the immunoassay by determining binding of the antibody reagent with a calibrator medium comprising recombinantly expressed BRCA2 fragment.

It will be understood that, the present method may be applied in combination with other routine methods for detecting cancer of interest. For example, a physician may use BRCA2 fragment biomarker blood values in combination with other diagnostic values and clinical observations to diagnose the onset of said cancer, and further to develop a course of treatment and therapy for each individual patient. It is also contemplated that monitoring blood levels of BRCA2 fragment biomarker will provide a means for monitoring the progress of a course of therapy for an individual patient.

In one embodiment the assay device is a mass spectrometer (e.g., U.S. Pat. No. 6,521,887, U.S. Pat. No. 6,541,768, U.S. Pat. No. 6,614,020). Mass spectrometric analysis of the low-molecular weight (LMW) range of the serum/plasma proteome has recently been used in the detection unknown peptides and protein fragments predicted to be derived from low-abundance proteins. Detailed investigation has led to an explanation on how such low abundance molecules are retained at detectable levels in the circulation, instead of being rapidly cleared and excreted. Theoretical models of biomarker production and association with serum carrier proteins have been developed to elucidate the mechanisms governing biomarker half-life in the bloodstream. These models predict that the vast majority of LMW biomarkers exist in association with circulating high molecular mass carrier proteins. Moreover, the total serum/plasma concentration of the biomarker is largely determined by the clearance rate of the carrier protein, not the free-phase biomarker clearance itself. These predictions have been verified experimentally using molecular mass fractionation of human serum before mass spectrometry sequence analysis.

Mass spectrometry therefore represents a well-accepted and reliable method for characterization of proteins. The method has great advantages in terms of high throughput, high accuracy, and high sensitivity in measurements, which is well suited for the identification of a wide variety of proteins and peptides, such those separated by 2D-PAGE and LC, and for the analysis of post-translational modifications, which play important roles in various biological events. Taking advantages of accumulating protein/DNA sequence databases, proteomic or peptidomic analysis of tissues and body fluid such as urine and blood has become one of the most important tasks that might lead to discovery of biomarkers.

The spectrometric methods used for the majority of biochemical analyses are Electrospray Ionisation (ESI) and Matrix Assisted Laser Desorption Ionisation (MALDI).

ESI technique, as generally known in the art, is well-suited to the analysis of polar molecules ranging from less than 100 Da to more than 1,000,000 Da in molecular mass. During standard electrospray ionisation the sample is dissolved in a polar, volatile solvent and pumped through a narrow, stainless steel capillary and a high voltage is applied to the tip of the capillary. Eventually charged sample ions, free from solvent, are released from the droplets, which pass through a small aperture into the analyzer of the mass spectrometer, which is held under high vacuum. The lens voltages are optimized individually for each sample. Electrospray ionisation is known as a "soft" ionisation method as the sample is ionised by the addition or removal of a proton, with very little extra energy remaining to cause fragmentation of the sample ions. Samples (M) with molecular weights greater than 1200 Da give rise to multiply charged molecular-related ions. Proteins have many suitable sites for protonation as all of the backbone amide nitrogen atoms could be protonated theoretically, as well as certain amino acid side chains such as lysine and arginine which contain primary amine functionalities.

On the other hand, Matrix Assisted Laser Desorption Ionisation (MALDI) deals well with thermolabile, non-volatile organic compounds especially those of high molecular mass and is used successfully in biochemical areas for the analysis of proteins, peptides, glycoproteins, oligosaccharides, and oligonucleotides. Most modern instruments are capable of measuring masses to within 0.01% of the molecular mass of the sample, at least up to 40,000 Da. MALDI is based on the bombardment of sample molecules with a laser light to bring about sample ionisation. The sample is pre-mixed with a highly absorbing matrix compound for the most consistent and reliable results, and a low concentration of sample to matrix works best. The matrix transforms the laser energy into excitation energy for the sample, which leads to sputtering of analyte and matrix ions from the surface of the mixture. In this way energy transfer is efficient and also the analyte molecules are spared excessive direct energy that may otherwise cause decomposition. MALDI is also a "soft" ionisation method and so results predominantly in the generation of singly charged molecular-related ions regardless of the molecular mass, hence the spectra are relatively easy to interpret. Fragmentation of the sample ions does not usually occur.

Tandem mass spectrometry (MS-MS) is used to produce structural information about a compound by fragmenting specific sample ions inside the mass spectrometer and identifying the resulting fragment ions. This information can then be pieced together to generate structural information regarding the intact molecule. Tandem mass spectrometry also enables specific compounds to be detected in complex mixtures on account of their specific and characteristic fragmentation patterns. The most common usage of MS-MS in biochemical areas is the ion scanning experiment which is particularly successful for peptide and nucleotide sequencing.

For use in Mass spectrometric analysis, peptides could be promptly isolated from blood by several batch-wise separation steps followed by LC, subjected to MALDI-MS/MS, and identified by database searching. The peptide profiles of blood can be analyzed using routine methods. In addition, a database search engine targeted to the analysis of peptides could be developed, which allows the setting of modes of fragmentations according to the propensities of fragment ions to be observed in MS/MS. Especially, high-energy CID spectra of peptides obtained by MALDI-MS/MS could be efficiently analyzed with a combination of the developed search engine and sequence database.

Although the description provided herein is of MALDI-TOF, it is conceivable to use any of the above-mentioned techniques for the analysis of biomarkers. Depending upon the nature of biological specimen and the sample itself, other routine proteomic techniques may also be employed.

Other routine methods for detecting peptidic biomarkers may comprise immunoassays. Any immunological method may be employed in the measurement of biomarker levels blood (e.g., serum or plasma). Typically, such measurement will be performed by sandwich immunoassays using two antibody reagents, one of which recognizes BRCA2 fragments to the exclusion of other related members of the BRCA family (e.g., BRCA1), while the other is capable of binding specifically or nonspecifically with the BRCA2 fragment. Assay format and methods for the preparation of the required antibody reagents can be selected by the skilled worker in the field. Suitable antibody reagents can be labeled, e.g., enzyme-labeled, or immobilized, e.g., coated onto a microtiter plate, bound to plastic or magnetic beads or particles, and can be comprised of whole immunoglobulins, e.g., IgG or IgM, or fragments, e.g., Fab, Fab', and F(ab').sub.2 fragments, or aggregates thereof.

One aspect of the instant invention relates to the diagnosis of breast cancer.

Breast cancer is the most common fatal malignancy in women. About 15% of all women will be diagnosed with breast cancer during their lifetime. In the United States, breast cancer is the third leading cause of death in women. Despite recent progress in early detection, as well as improved treatment, the mortality rate remains unchanged. Early diagnosis is the key to surviving breast cancer. Typically, the detection of breast cancer involves an exam by a physician, a mammogram, and either a needle aspiration or biopsy. When the breast tissue forming the lump is removed, the tissue is examined for possible cancer cells.

Analysis of the biochemical and cellular contents of breast ductal fluid has recently gained attention as a potential non-invasive method for studying the local microenvironment associated with the development and progression of breast cancer. Breast cancer arise from the ductal or lobular units of the breast. These units secrete into an average of six to nine ducts, and the secretions are easily accessible as they exit each breast through separate orifices at the nipple. In the instant invention, there is therefore provided a method for analyzing breast cancer biomarkers e.g., in breast ductal fluid of a patient. Using nipple aspiration, a simple and non-invasive procedure may be employed to obtain a concentrated fluid fraction of breast secretions. A skilled worker may then employ routine procedures, such as ones described previously, to analyze the presence and/or levels of BRCA2 biomarkers in the ductal fluid of said patients.

BRIEF DESCRIPTION OF THE DRAWINGS

Various features and attendant advantages of the present invention will be more fully appreciated as the same becomes better understood when considered in conjunction with the accompanying drawings, in which like reference characters designate the same or similar parts throughout the several views, and wherein:

FIG. 1. Schematic representation of the experimental technique. Raw serum is introduced into Millipore's Albumin depletion column. Albumin complexed with other proteins and peptides is retained. Following gentle washing under native conditions, the protein and peptide cargo is dissociated with organic solvent. Eluted proteins are fractionated by one-dimensional gel electrophoresis followed by in-gel trypsin digestion, and subjected to µLC-MS/MS analysis.

FIG. 2. Validation of BRCA2 peptide in serum. Panel A) The table lists the location of the four peptide sequences (SEQ ID NOS 1-4, respectively, in order of appearance) of BRCA2 found by mass spectrometry and the serum pool population origin. Panel B) A synthetic peptide corresponding to the amino acid sequence overlapping with the sequence found by mass spectrometry was used as an immuno-competition western blocking agent. All sequenced peptides (SEQ ID NOS 2-4 and 6, respectively, in order of appearance) are shown in a spatial orientation within native BRCA2. Identification of candidate proteins, which fall into putative functional categories previously known to be related to cancer, via single or multiple peptide hits.

Without further elaboration, it is believed that one skilled in the art, using the preceding description, can utilize the present invention to its fullest extent. The following preferred specific embodiments are, therefore, to be construed as merely illustrative, and not limitative of the remainder of the disclosure in any way whatsoever. The entire disclosure of all applications, patents and publications, cited above and in the figures are hereby incorporated by reference in their entirety.

In the forgoing and in the following examples, all temperatures are set forth uncorrected in degrees Celsius and, all parts and percentages are by weight, unless otherwise indicated.

EXAMPLES

The invention will be explained below with reference to the following non-limiting examples.

Example 1

Clinical Serum Samples

Serum samples were collected under full patient consent and IRB approval. Serum was collected prior to physical evaluation, diagnosis and treatment and stored at −80° C. The ovarian study set consisted of 40 unaffected "high risk" patient samples and 30 stage I, and 40 stage III ovarian cancer patients. The gynecologic oncology clinic where the cases were collected was in a separate but contiguously linked building from where the National Ovarian Cancer Early Detection Program (NOCEDP) at Northwestern University is located and where the high-risk controls were collected. A special attribute of this sample set is that the same personnel were involved with the blood collection, handling and storage of all biospecimens. In addition, all blood specimens were processed in an identical manner under the same methodology. Healthy control sera specimens from unaffected women determined to be at increased risk for ovarian cancer were enrolled in the NOCEDP and had no evidence of any cancer for 5 years as determined by bi-yearly 3D color Doppler ultrasound and extensive clinical evaluation by a board certified gynecologic oncologist. Increased risk was determined by classic genetic pedigree analysis and by the presence or absence of factors such as BRCA mutation status. Increased risk is based on computer generated risk algorithms such as BRCA Pro that are commercially available. All patients in the high risk clinic were seen by board certified genetic counselors and geneticists who define the risk. Similarly, only pre-operative case sera specimens procured in a gynecologic oncology clinic, were obtained from symptomatic women who were later surgically staged and found to have epithelial ovarian carcinoma. Each sample was accompanied by a verified pathologic diagnosis. Briefly, specimens were collected in red top vacutainer tubes and allowed to clot for one hour on ice, followed by spinning at 4° C. for 10 minutes at 3000 rpm.

The serum supernatant was divided in aliquots and stored at −80° C. until needed. Samples were selected for our analysis by random process categorized under cancer or benign pathologic diagnosis.

Native, diluted serum is introduced into an affinity column so that the carrier protein (albumin) is captured along with any bound molecules. The bound sub-proteome consisting of the carrier proteins and their peptide "cargo" is eluted, dissociated, and separated by one-dimensional gel electrophoresis. The entire gel lanes are cut out, finely subdivided into molecular mass regions, subjected to in-gel trypsin digestion, and prepared for electrospray mass spectrometric analysis.

Albumin and Bound Peptide Purification

Typically, 25 μL of human stage-specific (pooled) cancer sera (~3.1 mg protein) was diluted to 200 μL with Equilibration Buffer (Millipore) and run through a (Montage) albumin specific affinity column twice. The bound protein was washed thoroughly using two-200 μL volumes of proprietary wash buffer (provided by the manufacturer). These fractions were combined and labeled as a "flow-through" fraction. The bound proteins were eluted from the column by equilibrating with 70% Acetonitrile/30% $H_2O$/0.2% TFA for 30 minutes, followed by a slow spin-through of the elution mixture, repeated once. The eluate (retentate fraction) was lyophilized to <10 μL in a HetoVac roto (CT 110) and reconstituted in a 95% $H_2O$/5% Acetonitrile/0.1% formic acid buffer. Samples were desalted with a ZipTip cleanup and reconstituted in a 1:1 mixture of water and SDS sample buffer (20 μL total volume).

1D Protein Gel Separation and Digestion

The flow-through and retentate fractions were kept on ice in 20 μl sample buffer from 25 μL of original serum, then heated for 5 minutes at 95° C. and loaded onto 1D pre-cast gels to separate albumin from the proteins/peptides/fragments of interest. The proteins and fragments were visualized with a Gel Code Blue Stain Reagent (Pierce) following the manufacturer's protocols. The entire lane was excised from the gel and finely sliced into very small molecular weight regions (~35 slices/lane). Gel bands were reduced, alkylated, and digested with porcine modified trypsin following a standard protocol (26), and peptides were concentrated and prepped for mass spectrometry analysis.

Mass Spectrometry (μLC/MS/MS)

Samples were lyophilized to near dryness and reconstituted in 6.3 μL of Buffer A (95% $H_2O$, 5% Acetonitrile, 0.1% FA) for mass spectrometry analysis. Microcapillary reverse phase tandem mass spectrometry (μLC/MS/MS) analysis was performed using Dionex's LC Packings liquid chromatography system coupled on-line to a ThermoFinnigan LCQ Classic ion trap mass spectrometer (San Jose, Calif.) with a modified nanospray source. Reverse phase separations were performed with an in-house, slurry packed capillary column. The $C_{18}$ silica-bonded column was 75 μm i.d., 10 cm long fused silica packed with 5 μm beads with 300 angstrom pores (Vydac, Hesperia, Calif.). A μ-precolumn PepMap, 5 mm, $C_{18}$ cartridge (Dionex) acted as a desalting column. Sample was injected in μL pick-up mode and washed with Buffer A for five minutes prior to a linear gradient elution with Buffer B (95% Acetonitrile/5% $H_2O$/0.1% FA) up to 85% over 95 minutes at a flow rate of 200 nL/minute. Full MS scans were followed by four MS/MS scans of the most abundant peptide ions (in a data dependant mode) and collision induced dissociation (CID) was performed at a collision energy of 38% with the ion spray voltage set to 1.80 kV, capillary voltage and temperature to 22.80 V and 180° C., respectively.

Data Analysis and Repetitive Sequencing:

Data analysis was performed by searching MS/MS spectra against the European Bioinformatics Institute of the non-redundant proteome set of Swiss-Prot, TrEMBL and Ensembl entries through the Sequest Bioworks Browser (ThermoFinnigan) using a static modification of +57 Da on cysteine residues and a dynamic modification for oxidation of methionine of +15.9994 Da. Peptides were considered legitimate hits after filtering the correlation scores (refer below) and manual inspection of the MS/MS data. The criteria used to filter data in this embodiment are at least as stringent as most literature citations (17, 18, 27-30).

| Charge | $X_{corr}$ | ΔCn | Rsp |
|---|---|---|---|
| +1 | >1.9 | >0.1 = | 1 |
| +2 | >2.2 | >0.1 = | 1 |
| +3 | >3.5 | >0.1 = | 1 |

Accepted peptide hits were required to have an $X_{corr}$ ranking=1 relative to all other peptides in the database. The albumin extraction, gel electrophoresis, protein digestion/extraction, and μLC/MS/MS analysis was repeated in five subsequent trials—each time yielding diminishing returns of new identifications for low abundance peptide hits. Repetitive sequencing of peptides in multiple trials was a further means to validate the reproducibility of our experimental procedure—both within and between cancer stages.

Validation by Serum Western Blotting

The primary antibody that recognized BRCA2 was synthesized in-house. Rabbits were immunized with a peptide corresponding to an exact antigenic region of BRCA2 and the resulting polyclonal anti-BRCA2 antibody was affinity purified (see below). The specificity of the antibody was verified against the full-length (390 kDa) BRCA2 protein extracted from HeLa cell nuclear extract. Subsequent preincubation of the primary antibody with an immunizing synthetic peptide, overlapping the antigenic region of interest, successfully competed away the representative band of native BRCA2 at 390 kDa. After verification of the specificity of the antibody and competition peptide, this experimental procedure was applied to pooled ovarian cancer and control serum samples.

Prepared serum samples were heated for 5 minutes at 95° C. in sample buffer, 2% β-mercaptoethanol, followed by centrifugation at 10,000×g for 1 minute to remove insoluble material. Samples were then subjected to 1D electrophoresis and electroblotting at 30V for 2 hours, on ice. Membranes were incubated in 5% non-fat dry milk (NFDM), 7.5% glycine, and 0.1% Tween-20 in water overnight at 4° C. to block unoccupied protein binding sites.

The blocked membranes were rinsed two times with wash buffer (10 mmol/L Tris pH 7.5, 150 mmol/L NaCl, 0.1% BSA, and 0.1% Tween-20), then incubated in 1 μg/mL primary antibody (wash buffer with 5% NFDM) with rocking for 2 hours at room temperature. For peptide blocking/competition assays, 10 μg primary antibody was incubated with 100 μg corresponding immunization peptide in 400 μL wash buffer for 1 hour at room temperature with end-over-end mixing. The peptide-treated antibody solution was diluted to 10 mL (1 μg/mL final antibody concentration) in wash buffer with 5% NFDM before incubation with PVDF membrane.

The membranes were washed 5 times (3 minutes each) in 50 mL wash buffer and subsequently incubated in 10 mL of HRP-conjugated goat-anti-rabbit IgG (1:50,000 in wash buffer) for 1 hour at room temperature. After the PVDF membranes were washed thoroughly, signals were developed using enhanced chemiluminescence.

Peptide Specific Antibodies

A peptide representing amino acid residues 980-993 (DKIPEKNNDYMNKW) (SEQ ID NO: 5) of the BRCA-2 sequence was synthesized (Anaspec, San Jose, Calif.) and conjugated to Keyhole Limpet Hemocyanin for immunization as previously described (31). The resulting antisera were affinity purified over columns of peptides conjugated to Affigel 15 (Bio-Rad, Richmond, Calif.) and concentrated in stirred cells with YM-30 membranes (Millipore, Billerica, Mass.). The concentrates were subjected to gel filtration chromatography using 2.6×60 cm Superdex 200 columns (GE Healthcare, Piscataway, N.J.) in PBS, and the monomeric IgG fractions pooled and concentrated. The protein concentrations were determined by the Bradford assay (Bio-Rad, Richmond, Calif.).

Figure 1:
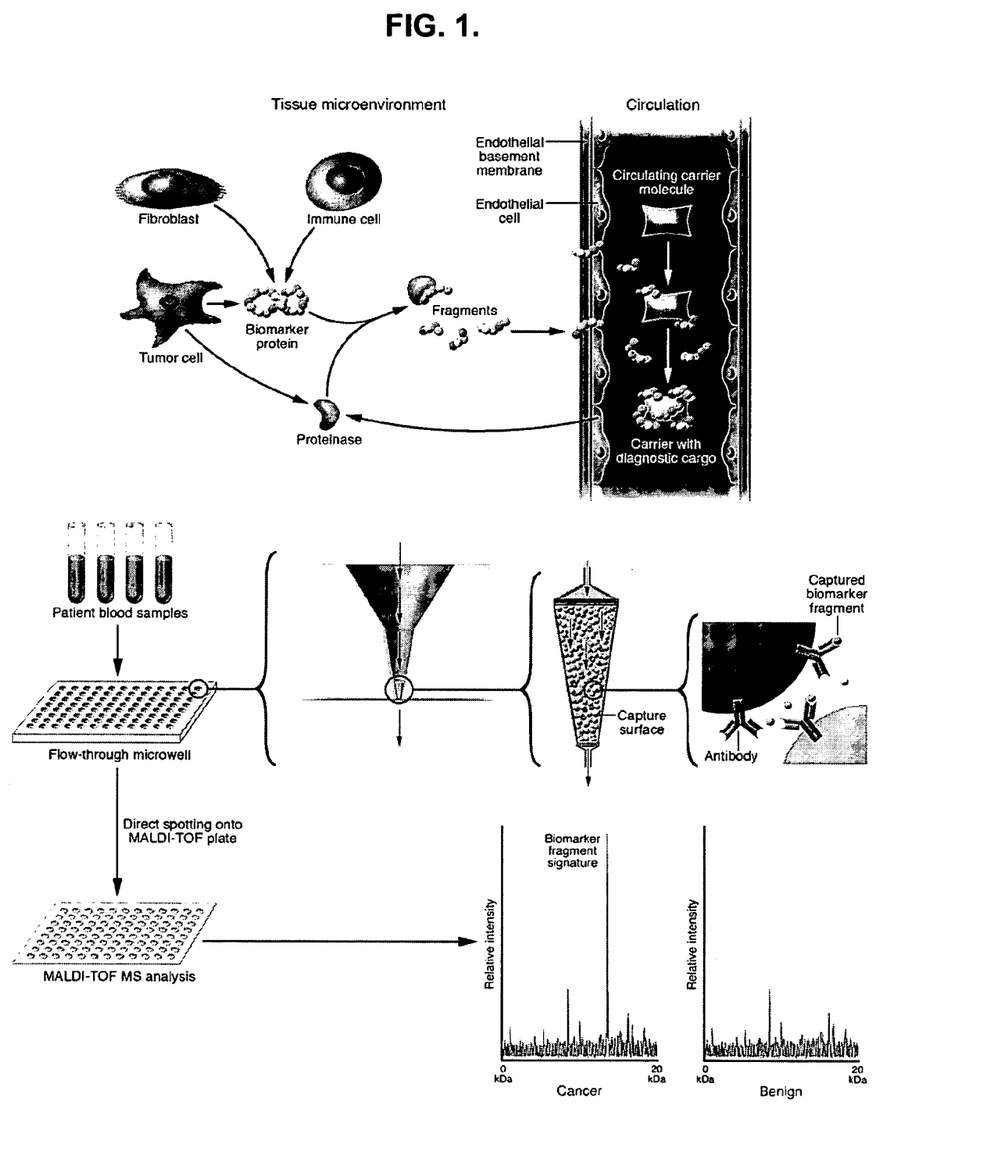
Figure 2:
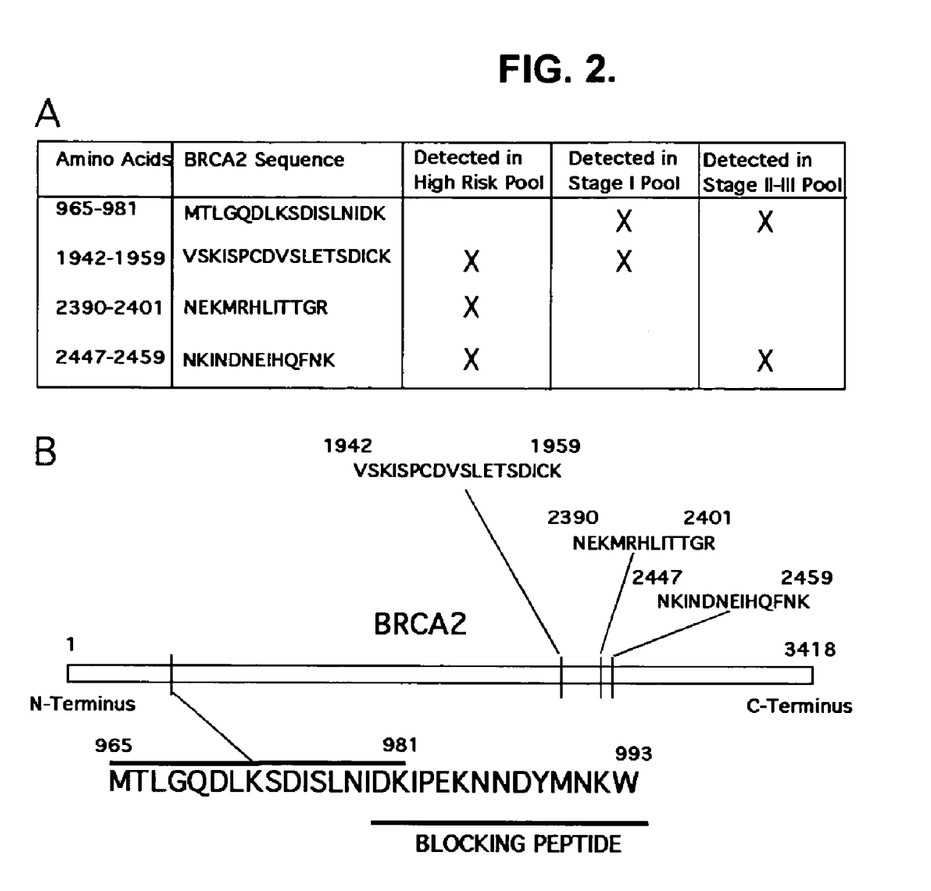

The ovarian cancer study set was divided according to disease category; serum samples within each disease category were pooled into sets. A total of 110 samples were pathologically classified into high risk (n=40), stage I (n=30), and stage III (n=40) ovarian cancer pools, and five separate aliquots per disease stage were iteratively sequenced by the experimental procedure in FIG. 1. A total of 1208 unique proteins were predicted in all three pools, 446 of these from multiple peptide sequences. An iterative sequencing approach examines the repetitive yield and variability between run and between stage classifications. The aggregate yield of low abundant protein identifications is expected to increase with repeated iterations of the experimental method. Table 1 describes the correlation between the number of sequencing iterations performed and the total number of peptide sequences, and corresponding protein identifications, obtained. Overall, the number of unique proteins identified by multiple peptide sequences increases at a diminishing rate relative to the number of iterations performed. FIG. 2 plots the rate of single and multiple peptide hits accumulated versus the number of experimental iterations. The ability to identify new peptides with multiple hits begins to diminish by the 3rd iteration (Table 1 and FIG. 2), however the total number of new peptide identifications and single hit identifications continues to rise even after 5 iterations. Previous work by Liu et al (32) revealed that saturation of new peptide identification occurs at around the 10th iteration. The results presented here show that greater coverage of lower abundant proteins can be achieved by increasing the number of experiments performed on a given sample.

Over 700 different tryptic peptides, derived from proteins not previously reported to exist in the blood in published data bases have been identified from various stages of ovarian cancer sera, many of which are of low abundance (Supplemental Table 1a-1c)). Over 100 proteins, which fall into putative functional categories previously known to be related to cancer, were identified by single or multiple peptide hits. In this study, unique single peptide hits were often discovered more than once from the same disease category. That is, the same single peptide hit was generated more than once from different aliquots of the same disease category.

Low abundance proteins or peptides derived from tissues entering the serum compartment can become complexed with high abundance proteins (3, 9-17, 32). At least half of all the proteins identified which are bound to albumin, and thereby sequenced using the present method, must exist as peptide fragments of whole proteins. This is supported by at least two points of evidence. First, the peptides are sequenced from a molecular weight region of a gel that does not correspond to the predicted mass of the intact protein. Second, passive diffusion of protein species through the vascular walls is hindered above apparent molecular weights of 60 kDa (25). Thus, large tissue proteins can only be represented in the blood circulation if they are actively secreted or if they are in-vivo cleavage products of the parent protein. BRCA-2, which has been sequenced with LC/MS/MS and represented by four distinct peptides (example BRCA-2 spectra from two iteratively found peptides is presented and subsequently validated by competition western blots, is not predicted to be in the blood circulation as an intact protein. In fact, the parent protein with a known molecular mass of 390 kDa was not found via serum western blotting. The figure shows immuno-competition of two cleavage products of BRCA2 at ~12 and 25 kDa that were identified in western blot analysis of pooled ovarian cancer sera. A synthetic peptide representing amino acid residues 980-993 (DKIPEKNNDYMNKW) (SEQ ID NO: 5) of the protein BRCA2 was immunized in a rabbit to produce a polyclonal antibody that ultimately detected the BRCA2 fragments in serum. Competition with the cognate peptide completely extinguished the 12 k and 25 kDa bands. The estimated mass of the immuno-fragments (12 and 25 kDa) represents less than 9% by mass of the total parent protein. Further, three other additional and distinct peptides were sequenced (residues 1942-1959, 2390-2401, and 2447-2459) in a separate region of the parent protein. The close proximity of the a.a. 2390-2401 and the a.a. 2447-2459 peptides suggest that they likely originate from a single serum fragment of BRCA-2.

The results suggests that at least two fragments of the BRCA2 parent protein exist in blood. A single predicted trypsin-cleaved peptide at amino acids 965-981 was identified in both stage I and stage III ovarian cancer serum pools. This peptide is represented in competition western blots by two distinct molecular weight bands. It is likely that a fragment containing the peptide at amino acids 965-981 would be cleaved at various residues in vivo, and could therefore be represented at multiple molecular weights. This peptide was not predicted in pooled high risk ovarian cancer serum by mass spectrometry analysis. Based on evidence from the western blots using a BRCA2 polyclonal antibody and the fact that BRCA2 is too large (390 kDa) to enter the blood circulation in its native form, we conclude that BRCA2 can be represented in the serum as one or more fragments, and that at least two amino terminal peptide fragments of BRCA2 less than 25 kDa can be validated by peptide competition for antibodies that recognize an amino acid sequence adjacent to, and overlapping with, the predicted peptide sequence. Additionally, two separate BRCA2 fragments encompassing no less than the amino acid region from 2390-2459 and 1942-1959 are predicted to exist in the serum from mass spectral evidence of multiple peptide sequences identified in this region of BRCA2.

BRCA2 is a well-studied tumor suppressor protein related to the p53 pathway that is directly implicated in familial breast cancer and ovarian cancer (45-48). Although the role of BRCA2 in breast and ovarian cancer predisposition is poorly understood, it is known that mutations of the BRCA2 gene are responsible for one-third of hereditary breast cancer cases (47). The figure suggests that at least two fragments of the BRCA2 parent protein exist in blood. A single predicted trypsin-cleaved peptide at amino acids 965-981 was identified in both stage I and stage III ovarian cancer serum pools. This peptide is represented in competition western blots by two distinct molecular weight bands. It is likely that a fragment containing the peptide at amino acids 965-981 would be cleaved at various residues in vivo, and could therefore be represented at multiple molecular weights. This peptide was not predicted in pooled high risk ovarian cancer serum by mass spectrometry analysis. Based on evidence from the western blots using a BRCA2 polyclonal antibody and the fact that BRCA2 is too large (390 kDa) to enter the blood circulation in its native form, we conclude that BRCA2 can be represented in the serum as one or more fragments, and that at least two amino terminal peptide fragments of BRCA2 less than 25 kDa can be validated by peptide competition for antibodies that recognize an amino acid sequence adjacent to, and overlapping with, the predicted peptide sequence. Additionally, two separate BRCA2 fragments encompassing no less than the amino acid region from 2390-2459 and 1942-1959 are predicted to exist in the serum from mass spectral evidence of multiple peptide sequences identified in this region of BRCA2.

Representative tandem mass spectra of BRCA2 peptides. Results show the result for the BRCA2 peptide identified as MTLGQDLKSDISLNIDK (SEQ ID NO: 1) and the result for the BRCA2 peptide identified as VSKISPCDVSLETSDICK (SEQ ID NO: 2).

The table lists the location of the four peptide sequences of BRCA2 found by mass spectrometry and the serum pool population origin. A synthetic peptide corresponding to the amino acid sequence overlapping with the sequence found by mass spectrometry was used as an immuno-competition western blocking agent. All sequenced peptides are shown in a spatial orientation within native BRCA2. The peptide identification by mass spectrometry was confirmed by competitive western blot analysis using the peptide shown. Western blots of pooled ovarian cancer are displayed in a dilution curve. A standard western blot using a polyclonal anti-rabbit primary antibody synthesized in-house corresponding to the antigenic region of BRCA2 found by mass spectrometry is represented. The primary antibody is first incubated with a competition peptide specific for the identical amino acid region of BRCA2 prior to western blot. Another antibody is a negative control/background of the goat-anti rabbit secondary. The BRCA2 peptides highlighted are evident at ~12 and 25 kDa. The indication of peptide fragments in western blots from serum is expected due to the fact that the molecular weight of the parent BRCA2 protein is 390 kDa, an apparent mass much larger than what is known to be able to passively enter the blood stream. Western blot using polyclonal anti-BRCA 2 antibodies of two example ovarian cancer sera, compared to total nuclear lysate of Hela cells (HNL). Absence of the full length BRCA2 protein in the sera is shown.

A large number of candidate ovarian cancer specific peptides have been found. Sequencing these peptides indicates that they are fragments of low abundance molecules such as BRCA2, tyrosine kinases and signaling molecules, and intracellular scaffolding proteins. Thus, the endogenous circulation "fragmentome" may be potentially redefined as a subset of the "interactome". Identification of the components of the LMW circulatory proteome creates information that transcends whether or not a particular type of measurement technology, such as MALDI-TOF, is employed. Regardless of the ultimate composition of the LMW archive, whether or not information comes from the in vivo tissue/microenvironment sources or from ex vivo generation, this invention is highly useful in the diagnostics field or described.

Currently, existing immunoassay platforms cannot measure panels of fragment analytes. This is because immunoassays, by their very definition, rely on antibody based capture and detection. An antibody-based assay cannot distinguish the "parent" molecule from its clipped fragments (that contains the diagnostic information) since the antibody recognizes its cognate epitope in both the parent and fragment molecule. Thus, the future of fragment-based diagnostics requires methods of this invention that read out both the identity and the exact size of the molecule (its fragment characteristic). Immuno-MS is one example of how this could occur. With this approach, a micro affinity antibody column, e.g., in multiplexed microwell format, can first be used to capture all species of molecules that contain the antibody recognition site. Next, the captured fragments are eluted off the antibody column directly into a MS (such as a MALDI-TOF). MS analysis of the eluted peptides provides an extremely accurate mass determination of the entire population of captured peptides. Thus, in only two steps, a panel of peptide fragments derived from a known parent molecule can be rapidly tabulated per this invention by immuno-MS.

BRIEF DESCRIPTION OF THE TABLES

Table 1: Representation of the total number of peptide hits and protein identifications acquired after subsequent iterations of the experimental method for ovarian cancer stage-specific and normal sera.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

It is believed that one skilled in the art, using the preceding information and information available in the art, can utilize the present invention to its fullest extent. It should be apparent to one of ordinary skill in the art that changes and modifications can be made to this invention without departing from the spirit or scope of the invention as it is set forth herein. The topic headings set forth above and below are meant as guidance where certain information can be found in the application, but are not intended to be the only source in the application where information on such topic can be found. All publications and patents cited above are incorporated herein by reference.

TABLE 1

Representation of the total number of peptide hits and protein identifications acquired after subsequent iterations of the experimental method for ovarian cancer stage-specific and normal sera. The number of patient samples pooled for each group is indicated. Five iterations for each category were performed and report the total number of peptides sequenced correlating to the total number of unique proteins identified. Protein IDs are classified as single or multiple peptide hits.

| | n value (# of patient samples in pool) | # of iterations | # of unique protein ID'S | # peptides sequenced | # of multi-peptide protein ID'S | # of single peptide protein IDs |
|---|---|---|---|---|---|---|
| | Ovarian Cancer Pool | | | | | |
| | | 5 | 359 | 935 | 147 | 212 |
| | | 4 | 334 | 908 | 144 | 190 |
| High Risk | 40 | 3 | 282 | 838 | 140 | 142 |
| | | 2 | 235 | 720 | 133 | 102 |
| | | 1 | 164 | 565 | 106 | 58 |
| | | 5 | 453 | 1027 | 149 | 304 |
| | | 4 | 425 | 998 | 148 | 277 |

TABLE 1-continued

Representation of the total number of peptide hits and protein identifications acquired after subsequent iterations of the experimental method for ovarian cancer stage-specific and normal sera. The number of patient samples pooled for each group is indicated. Five iterations for each category were performed and report the total number of peptides sequenced correlating to the total number of unique proteins identified. Protein IDs are classified as single or multiple peptide hits.

| | n value (# of patient samples in pool) | # of iterations | # of unique protein ID'S | # peptides sequenced | # of multi-peptide protein ID'S | # of single peptide protein IDs |
|---|---|---|---|---|---|---|
| | | | Ovarian Cancer Pool | | | |
| Stage I | 30 | 3 | 386 | 921 | 142 | 244 |
| | | 2 | 298 | 732 | 132 | 166 |
| | | 1 | 168 | 594 | 111 | 57 |
| | | 5 | 396 | 896 | 150 | 246 |
| | | 4 | 358 | 848 | 148 | 210 |
| Stage III-IV | 40 | 3 | 301 | 761 | 144 | 157 |
| | | 2 | 253 | 694 | 140 | 113 |
| | | 1 | 185 | 560 | 123 | 62 |

LITERATURE CITED

1. Ardekani A M, Liotta L A, Petricoin E F 3rd. Clinical potential of proteomics in the diagnosis of ovarian cancer. Expert Rev Mol Diagn 2002; 2(4): 312-20.
2. Anderson N L, Anderson N G. The human plasma proteome: history, character, and diagnostic prospects. Mol Cell Proteomics 2002; 1(11): 845-67.
3. Mehta A I, Ross S, Lowenthal M S, Fusaro V, Fishman D A, Petricoin E F 3rd, Liotta L A. Biomarker amplification by serum carrier protein binding. Dis Markers 2003; 19(1): 1-10.
4. Adkins J N, Varnum S M, Auberry K J, Moore R J, Angell N H, Smith R D, Springer D L, Pounds J G. Toward a human blood serum proteome: analysis by multidimensional separation coupled with mass spectrometry. Mol Cell Proteomics 2002; 1(12): 947-55.
5. Pieper R, Su Q, Gatlin C L, Huang S T, Anderson N L, Steiner S. Multi-component immunoaffinity subtraction chromatography: an innovative step towards a comprehensive survey of the human plasma proteome. Proteomics 2003; 3(4): 422-32.
6. Rothemund D L, Locke V L, Liew A, Thomas T M, Wasinger V, Rylatt, D B. Depletion of the highly abundant protein albumin from human plasma using the Gradiflow. Proteomics 2003; 3(3): 279-87.
7. Wang Y Y, Cheng P, Chan D W. A simple affinity spin tube filter method for removing high-abundant common proteins or enriching low-abundant biomarkers for serum proteomic analysis. Proteomics 2003; 3(3): 243-8.
8. Pieper R, Gatlin C L, Makusky A J, Russo P S, Schatz C R, Miller S S, Su Q, McGrath A M, Estock M A, Parmar P P, Zhao M, Huang S T, Zhou J, Wang F, Esquer-Blasco R, Anderson N L, Taylor J, Steiner S. The human serum proteome: display of nearly 3700 chromatographically separated protein spots on two-dimensional electrophoresis gels and identification of 325 distinct proteins. Proteomics 2003; 3(7): 1345-64.
9. Dennis M S, Zhang M, Meng Y G, Kadkhodayan M, Kirchhofer D, Combs D, Damico L A. Albumin binding as a general strategy for improving the pharmacokinetics of proteins. J Biol Chem 2002; 277(38): 35035-43.
10. Lee V H L. Peptide and Protein Drug Delivery. New York: Lee V H L, ed. Marcel Dekker, 1990. pp 1-56.
11. Makrides S C, Nygren P A, Andrews B, Ford P J, Evans K S, Hayman E G, Adari H, Uhlen M, Toth C A. Extended in vivo half-life of human soluble complement receptor type 1 fused to a serum albumin-binding receptor. J Pharmacol Exp Ther. 1996; 277(1): 534-42.
12. Kurtzhals P, Havelund S, Jonassen I, Kiehr B, Larsen U D, Ribel U, Markussen J. Albumin binding of insulins acylated with fatty acids: characterization of the ligand-protein interaction and correlation between binding affinity and timing of the insulin effect in vivo. Biochem J. 1995; 15(312, Pt 3): 725-31.
13. Markussen J, Havelund S, Kurtzhals P, Andersen A S, Halstrom J, Hasselager E, Larsen U D, Ribel U, Schaffer L, Vad K, Jonassen I. Soluble, fatty acid acylated insulins bind to albumin and show protracted action in pigs. Diabetologia 1996; 39(3): 281-8.
14. Gordon L M, Curtain C C, McCloyn V, Kirkpatrick A, Mobley P W, Waring A J. The amino-terminal peptide of HIV-1 gp41 interacts with human serum albumin. AIDS Res Hum Retroviruses 1993; 9(11): 1145-56.
15. Sjobring U, Falkenberg C, Nielsen E, Akerstrom B, Bjorck L. Isolation and characterization of a 14-kDa albumin-binding fragment of streptococcal protein G. The Journal of Immunology 1988; 140(5): 1595-1599.
16. Raghu P, Sivakumar B. Interactions amongst plasma retinol-binding protein, transthyretin and their ligands: implications in vitamin A homeostasis and transthyretin amyloidosis. Biochim Biophys Acta. 2004; 1703(1):1-9.
17. Tirumalai R S, Chan K C, Prieto D A, Issaq H J, Conrads T P, Veenstra T D. Characterization of the low molecular weight human serum proteome. Mol Cell Proteomics 2003; 2(10): 1096-103.
18. Zhou M, Lucas D A, Chan K C, Issaq H J, Petricoin E F 3rd, Liotta L A, Veenstra T D, Conrads T P. An investigation into the human serum "interactome". Electrophoresis 2004; 25(9): 1289-98.
19. Corot C, Violas X, Robert P, Gagneur G, Port M. Comparison of different types of blood pool agents (P792, MS325, USPIO) in a rabbit MR angiography-like protocol. Invest Radiol 2003; 38(6): 311-9.
20. Dufour C, Dangles O. Flavonoid-serum albumin complexation: determination of binding constants and binding sites by fluorescence spectroscopy. Biochim Biophys Acta 2005; 1721(1-3): 164-73.
21. Ding Y, Lin B, Huie C W. Binding studies of porphyrins to human serum albumin using affinity capillary electrophoresis. Electrophoresis 2001; 22(11): 2210-6.
22. In Drug information for the health care professional, United States Pharmacopeial Convention, Inc. Englewood, Colo.: Micromedex, 2000.
23. Peters T Jr. Serum albumin. The plasma proteins: structure, function, and genetic control. 2nd ed. New York: Academic Press, 1975: Vol. 1, pp 133-181.
24. Rainey T G, Read C A. Pharmacology of colloids and crystalloids, the pharmacologic approach to the critically ill patient. 3rd ed. Baltimore: Williams & Wilkins, 1994: Vol. 1, p 272-290.
25. Wagner B K, D'Amelio L F. Pharmacologic and clinical considerations in selecting crystalloid, colloidal, and oxygen-carrying resuscitation fluids, Part 1. Clin Pharm 1993; 12(5): 335-46.
26. Kinter M, Sherman N E. Protein Sequencing and Identification Using Tandem Mass Spectrometry. In ed. New York: Wiley-Interscience, Inc., 2000: pp.xvi+301.

27. Peng J, Elias J E, Thoreen C C, Licklider L J, Gygi S P. Evaluation of multidimensional chromatography coupled with tandem mass spectrometry (LC/LC-MS/MS) for large-scale protein analysis: the yeast proteome. J Proteome Res 2003; 2(1): 43-50.
28. Qian W J, Liu T, Monroe M E, Strittmatter E F, Jacobs J M, Kangas L J, Petritis K, Camp D G 2$^{nd}$, Smith R D. Probability-based evaluation of peptide and protein identifications from tandem mass spectrometry and SEQUEST analysis: the human proteome. J Proteome Res 2005; 4(1): 53-62.
29. Wilmarth P A, Riviere M A, Rustvold D L, Lauten J D, Madden T E, David L L. Two-dimensional liquid chromatography study of the human whole saliva proteome. J Proteome Res 2004; 3(5): 1017-23.
30. Xiang R, Shi Y, Dillon D A, Negin B, Horvath C, Wilkins J A. 2D LC/MS analysis of membrane proteins from breast cancer cell lines MCF7 and BT474. J Proteome Res 2004; 3(6): 1278-83.
31. Goldsmith P, Backlund P S Jr, Rossiter K, Carter A, Milligan G, Unson C G, Spiegel A. Purification of heterotrimeric GTP-binding proteins from brain: identification of a novel form of Go. Biochemistry 1988; 27(18): 7085-90.
32. Liu H, Sadygov R G, Yates J R. A model for random sampling and estimation of relative protein abundance in shotgun proteomics. Anal Chem 2004. 76:4193-4201).
33. Moss E L, Hollingworth J, Reynolds T M. The role of CA125 in clinical practice. J Clin Pathol 2005; 58(3): 308-12.
34. Topley N, Michael D, Bowen T. CA125: Holy Grail or a Poisoned Chalice. Nephron Clin Pract 2005; 100(2): c52-c54.
35. Washburn, M. P., Wolters, D., Yates, J. R. 3rd. (2001) Large-scale analysis of the yeast proteome by multidimensional protein identification technology, *Nat. Biotechnol.* 19, 242-7.
36. Adkins, J. N., Varnum, S. M., Auberry, K. J., Moore, R. J., Angell, N. H., Smith, R. D., Springer, D. L., Pounds, J. G. (2002) *Mol. Cell. Proteomics* 1, 947-955.
37. Yu, L. R., Conrads, T. P., Uo, T., Morrison, R. S., Chan, K., Lucas, D. A., Blonder, J., Issaq, H. J. and Veenstra, T. D. (2004) Global Analysis of the Cortical Neuron Proteome, *Mol. Cell. Proteomics* 3, 896-907.)
38. Veenstra T D, Conrads T P, Issaq H J. What to do with "one-hit wonders"? Electrophoresis, 2004; 25(9): 1278-9.
39. Peng, J., Elias, J. E., Thoreen, C. C., Licklider, L. J., Gygi, S. P. (2003) *J. Proteome Res.* 2, 43-50.
40. Johnson, M. D., Yu, L-R, Conrads, T. P., Kinoshito, Y., Uo, T., Lee, S-W., Smith, R. D., Veenstra, T. D., and Morrison, R. S. (2004) Proteome Analysis of DNA Damage-Induced Neuronal Death using High Throughput Mass Spectrometry, *J. Biol. Chem.* 279, 26685-26697.
41. Conrads, K. A., Yi, M., Simpson, K. A., Stevens, R., Lucas, D. A., Veenstra, T. D., Conrads, T. P., and Beck, G. R. Jr. (2005) A Combined Proteome and Microarray Investigation of Inorganic Phosphate-induced Pre-osteoblast Cells *Mol. Cell. Proteomics*, in press.
42. Ballif, B. A., Villen, J., Beausoleil, S. A., Schwartz, D. and Gygi, S. P. (2004) Phosphoproteomic Analysis of the Developing Mouse Brain, *Mol Cell Proteomics* 3, 1093-1101.
43. Hardwidge, P. R., Rodriguez-Escudero, I., Goode, D., Donohoe, S., Eng, J., Goodlett, D. R., Aebersold R., Finlay, B. B., *J. Biol. Chem.* 2004, 279, 20127-
44. Anderson, L. (2005) Candidate-based proteomics in the search for biomarkers of cardiovascular disease, *J. Physiol.* 563, 23-60.
45. Jonkers J, Meuwissen R, van der Gulden H, Peterse H, van der Valk M, Berns A. Synergistic tumor suppressor activity of BRCA2 and p53 in a conditional mouse model for breast cancer. Nat Genet. 2001; 29(4): 418-25.
46. Esashi F, Christ N, Gannon J, Liu Y, Hunt T, Jasin M, West S. CDK-dependent phosphorylation of BRCA2 as a regulatory mechanism for recombinational repair. Nature 2005; 434(7033): 598-604.
47. Ford D, Easton D F, Stratton M, Narod S, Goldgar D, Devilee P, et al. Genetic heterogeneity and penetrance analysis of the BRCA1 and BRCA2 genes in breast cancer families. The Breast Cancer Linkage Consortium. Am J Hum Genet. 1998; 62(3): 676-89.
48. Hussain S, Witt E, Huber P, Medhurst A, Ashworth A, Mathew C. Direct interaction of the Fanconi anaemia protein FANCG with BRCA2/FANCD1. Human Molecular Genetics 2003; 12(19): 2503-2510.
49. Lancaster J M, Wooster R, Mangion J.; Phelan C M, Cochran C, Gumbs C, Seal S, Barfoot R, Collins N, Bignell G, Patel S, Hamoudi R, Larsson C, Wiseman R W, Berchuck A, Iglehart J D, Marks J R, Ashworth A, Stratton M R, Futreal P R. BRCA2 mutations in primary breast and ovarian cancers. Nature Genet. 1996; 13: 238-240.
50. Garcia-Marco J A, Caldas C, Price C M, Wiedemann L M, Ashworth A, Catovsky D. Frequent somatic deletion of the 13q12.3 locus encompassing BRCA2 in chronic lymphocytic leukemia. Blood 1996; 88: 1568-1575.
51. Edwards S M, Kote-Jarai Z, Meitz J, Hamoudi R, Hope Q, Osin P, Jackson R, Southgate C, Singh R, Falconer A, Dearnaley D P, Ardern-Jones A et al. Two percent of men with early-onset prostate cancer harbor germline mutations in the BRCA2 gene. Am. J. Hum. Genet. 2003; 72:1-12.
52. Schutte M, da Costa L T, Hahn S A, Moskaluk C, Hoque A, Rozenblum E, Weinstein C L, Bittner M, Meltzer P S, Trent J M, Yeo C J, Hruban R H, Kern S E, Identification by representational difference analysis of a homozygous deletion in pancreatic carcinoma that lies with the BRCA2 region. Proc. Nat. Acad. Sci. 1995; 92: 5950-5954.

We claim:

1. A method of detecting ovarian cancer in a subject, comprising detecting the presence or absence of a fragment of a full-length molecule of a BRCA2 polypeptide, wherein the fragment comprises amino acids 965-981 of said BRCA2 and is correlated with the presence of ovarian cancer in said subject.

2. A method of claim 1, wherein the fragment is a proteolytic fragment comprising amino acids 965-981 of said BRCA2.

3. A method of claim 1, wherein the fragment comprises a tryptic fragment comprising amino acids 965-981 of said BRCA2.

4. A method of claim 1, wherein said fragment is a product of trypsin digestion.

5. A method of claim 1, further comprising capturing said fragment using an affinity ligand which is specific to said fragment, and then detecting said fragment using mass spectroscopy.

6. A method of claim 1, wherein said fragment is detected as an about 12 kDa and 25 kDa fragment.

7. A method of claim 1, further comprising detecting the presence or absence of a fragment of a full-length molecule of BRCA2, wherein the fragment is a proteolytic fragment comprising amino acids 1942-1959 of said BRCA2.

8. A method of claim 1, further comprising detecting the presence or absence of a fragment of a full-length molecule of BRCA2, wherein the fragment is a proteolytic fragment comprising amino acids 2447-2459 of said BRCA2.

9. A method of claim 7, wherein the presence of 965-981 and 1942-1959 containing BRCA2 fragments indicate that said subject has Stage I ovarian cancer.

10. A method of claim 8, wherein the presence of 965-981 and 2447-2459 containing BRCA2 fragments indicates that said subject has Stage III ovarian cancer.

11. A method of claim 1, wherein said fragment is bound to serum albumin.

12. A method of claim 1, wherein said fragment is detected using mass spectroscopy.

13. A method of claim 1, wherein the presence of the fragment is correlated with a particular stage of ovarian cancer.

* * * * *

SEQUENCE LISTING

<160> NUMBER OF SEQ ID NOS: 6

<210> SEQ ID NO 1
<211> LENGTH: 17
<212> TYPE: PRT
<213> ORGANISM: Homo sapiens

<400> SEQUENCE: 1

-continued

```
Met Thr Leu Gly Gln Asp Leu Lys Ser Asp Ile Ser Leu Asn Ile Asp
1               5                   10                  15

Lys

<210> SEQ ID NO 2
<211> LENGTH: 18
<212> TYPE: PRT
<213> ORGANISM: Homo sapiens

<400> SEQUENCE: 2

Val Ser Lys Ile Ser Pro Cys Asp Val Ser Leu Glu Thr Ser Asp Ile
1               5                   10                  15

Cys Lys

<210> SEQ ID NO 3
<211> LENGTH: 12
<212> TYPE: PRT
<213> ORGANISM: Homo sapiens

<400> SEQUENCE: 3

Asn Glu Lys Met Arg His Leu Ile Thr Thr Gly Arg
1               5                   10

<210> SEQ ID NO 4
<211> LENGTH: 13
<212> TYPE: PRT
<213> ORGANISM: Homo sapiens

<400> SEQUENCE: 4

Asn Lys Ile Asn Asp Asn Glu Ile His Gln Phe Asn Lys
1               5                   10

<210> SEQ ID NO 5
<211> LENGTH: 14
<212> TYPE: PRT
<213> ORGANISM: Homo sapiens

<400> SEQUENCE: 5

Asp Lys Ile Pro Glu Lys Asn Asn Asp Tyr Met Asn Lys Trp
1               5                   10

<210> SEQ ID NO 6
<211> LENGTH: 29
<212> TYPE: PRT
<213> ORGANISM: Homo sapiens

<400> SEQUENCE: 6

Met Thr Leu Gly Gln Asp Leu Lys Ser Asp Ile Ser Leu Asn Ile Asp
1               5                   10                  15

Lys Ile Pro Glu Lys Asn Asn Asp Tyr Met Asn Lys Trp
                20                  25
```